US007182738B2

(12) United States Patent
Bonutti et al.

(10) Patent No.: US 7,182,738 B2
(45) Date of Patent: Feb. 27, 2007

(54) PATIENT MONITORING APPARATUS AND METHOD FOR ORTHOSIS AND OTHER DEVICES

(75) Inventors: Peter M. Bonutti, Effingham, IL (US); Justin E. Beyers, Chicago, IL (US)

(73) Assignee: Marctec, LLC, Effingham, IL (US)

( * ) Notice: Subject to any disclaimer, the term of this patent is extended or adjusted under 35 U.S.C. 154(b) by 617 days.

(21) Appl. No.: 10/421,965

(22) Filed: Apr. 23, 2003

(65) Prior Publication Data

US 2004/0215111 A1    Oct. 28, 2004

(51) Int. Cl.
*A61H 1/00*    (2006.01)

(52) U.S. Cl. .............................. 601/5; 601/23; 601/33; 601/DIG. 19; 601/DIG. 23

(58) Field of Classification Search .................... 601/5, 601/23, 33, 34, 35; 602/5, 16, 19, 23, 26; 600/547, 595; 607/48, 49; 482/8, 902; 73/379.01
See application file for complete search history.

(56) References Cited

U.S. PATENT DOCUMENTS

| | | | |
|---|---|---|---|
| 4,807,601 A | 2/1989 | Wright | |
| 5,052,375 A | 10/1991 | Stark | |
| 5,167,612 A | 12/1992 | Bonutti | |
| 5,201,772 A | 4/1993 | Maxwell | |
| 5,213,094 A | 5/1993 | Bonutti | |
| 5,252,102 A | 10/1993 | Singer et al. | |
| 5,285,773 A | 2/1994 | Bonutti | |
| 5,365,947 A | 11/1994 | Bonutti | |
| 5,395,303 A * | 3/1995 | Bonutti et al. | 602/16 |
| 5,452,205 A * | 9/1995 | Telepko | 601/5 |
| 5,453,075 A | 9/1995 | Bonutti et al. | |
| 5,456,268 A | 10/1995 | Bonutti | |
| 5,503,619 A | 4/1996 | Bonutti | |
| 5,535,274 A * | 7/1996 | Braitberg et al. | 379/446 |
| 5,538,486 A | 7/1996 | France et al. | |
| 5,611,764 A | 3/1997 | Bonutti et al. | |
| 5,626,537 A | 5/1997 | Danyo et al. | |
| 5,685,830 A | 11/1997 | Bonutti | |
| 5,823,975 A | 10/1998 | Stark et al. | |
| 5,848,979 A | 12/1998 | Bonutti et al. | |
| 5,929,782 A * | 7/1999 | Stark et al. | 601/34 |
| 5,980,435 A | 11/1999 | Joutras et al. | |
| 6,059,576 A | 5/2000 | Brann | |
| 6,113,562 A | 9/2000 | Bonutti et al. | |
| 6,184,797 B1 | 2/2001 | Stark et al. | |
| 6,296,595 B1 | 10/2001 | Stark et al. | |
| 6,371,123 B1 | 4/2002 | Stark et al. | |
| 6,384,755 B1 * | 5/2002 | Hayden | 341/120 |
| 6,436,058 B1 | 8/2002 | Krahner et al. | |
| 6,502,577 B1 | 1/2003 | Bonutti | |
| 6,509,659 B1 * | 1/2003 | Carroll et al. | 307/125 |
| 6,890,285 B2 * | 5/2005 | Rahman et al. | 482/8 |
| 2001/0047209 A1 | 11/2001 | Soloman | |
| 2002/0029784 A1 | 3/2002 | Stark | |
| 2002/0183655 A1 | 12/2002 | Zhang | |

* cited by examiner

*Primary Examiner*—Quang D. Thanh
(74) *Attorney, Agent, or Firm*—Fleit Kain Gibbons Gutman Bongini & Bianco; Paul D. Bianco; Martin Fleit

(57) ABSTRACT

A monitoring system for monitoring a patient using a device, such as an orthosis system is provided. The system includes a monitor that can be incorporated or otherwise coupled to the device. The monitor can have a position sensor, a temperature sensor, and a device type sensor for monitoring the patient's implementation of a protocol. The data obtained from the monitor can be remotely analyzed by a healthcare professional and the protocol can be adjusted accordingly.

15 Claims, 9 Drawing Sheets

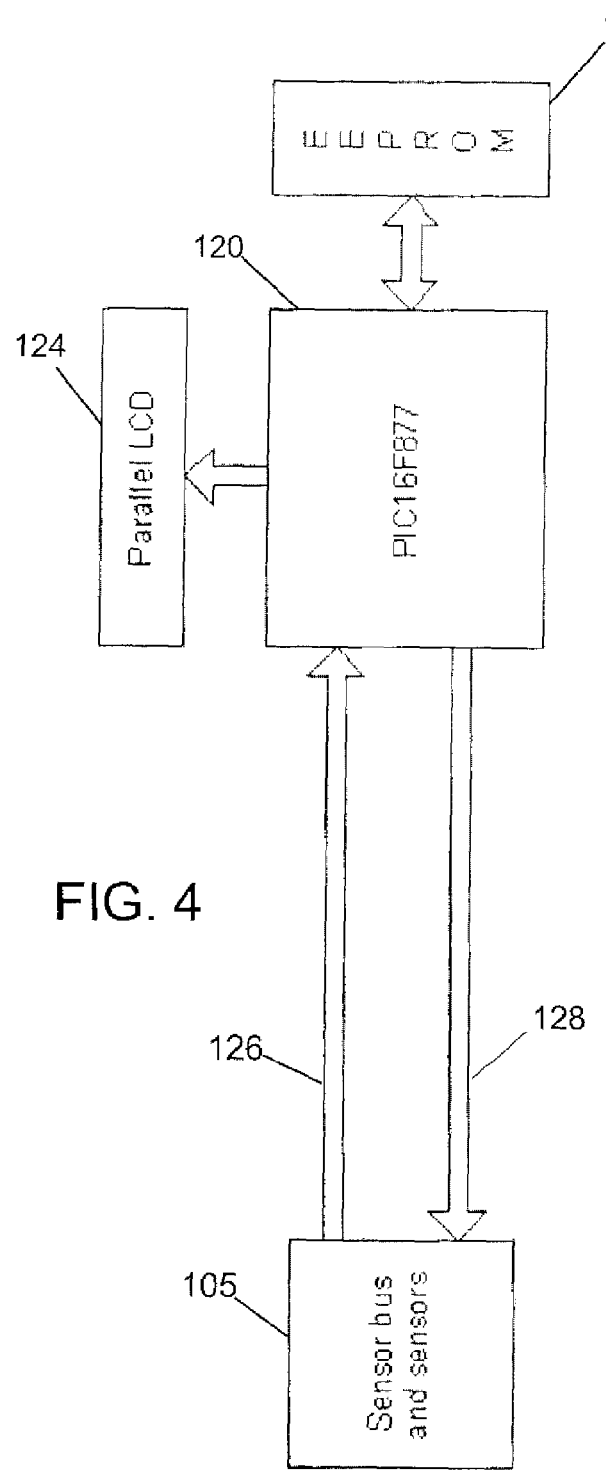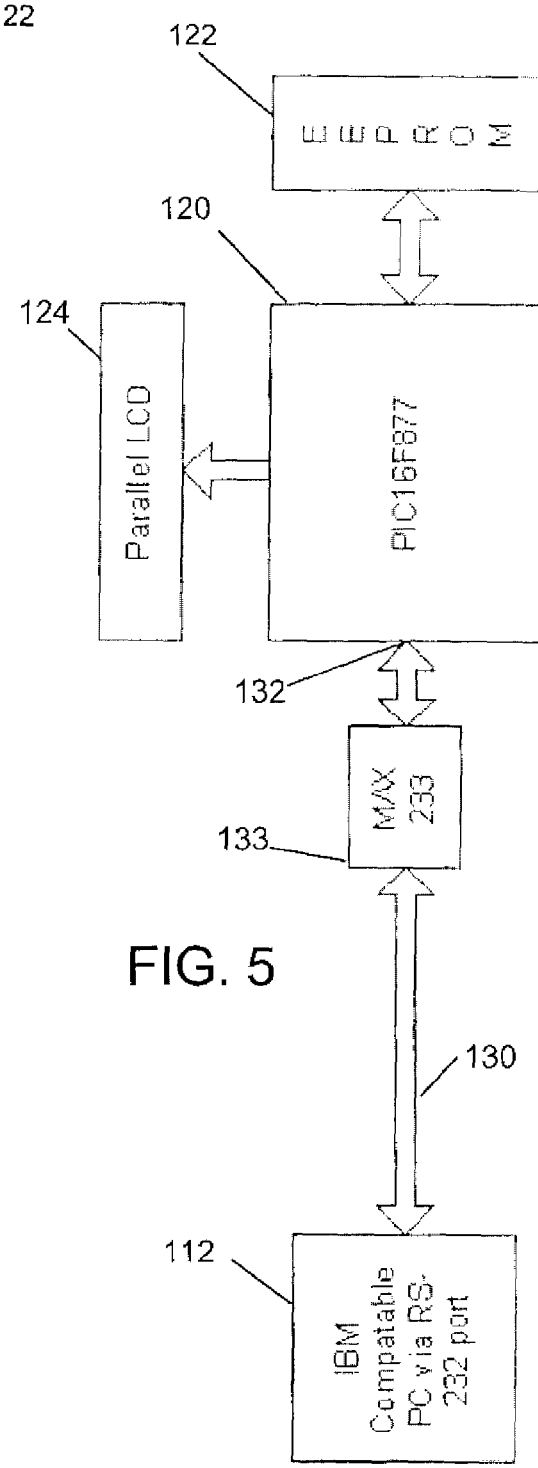

PATIENT MONITORING APPARATUS AND METHOD FOR ORTHOSIS AND OTHER DEVICES

BACKGROUND OF THE INVENTION

1. Field of the Invention

The present invention relates to a patient monitoring system and method that can be used, for example, with an orthosis for physical therapy.

2. Description of Related Art

In the field of medicine, rehabilitation after surgery or other major medical procedures has been an important issue for researchers. As shown in U.S. Pat. Nos. 5,395,303; 5,285,773; 5,213,094; 5,167,612; 6,502,577; 6,113,562 and 5,848,979, continuous passive motion has been used to treat conditions such as the glenohumeral joint adhesive capsulitis. These patents teach using stretching principles in order to treat one of the major problems patients are referred to physical therapists for: lack of a full range of motion in their joints. The orthosis devices of these patents simulate manual therapy techniques used in clinical settings, combining the principles of stress relaxation and progressive stretch to achieve permanent elongation of soft tissue.

Once a patient has been prescribed treatment with one of the rehabilitation orthosis devices, a major concern is patient education and compliance. To maximize improvement in range of motion the patient must comply with the prescribed protocol and the patient improvement must be tracked. The exercise protocol for these orthosis devices is well established, and should be followed closely to ensure the best treatment possible. First, the patient fits the orthosis as specified by the device specific instructions. Then the patient rotates the knob of the orthosis device until a slight stretch is felt. This stretch should not be painful. Now the patient holds this position for a predetermined time period (e.g., five minutes), and then this procedure is repeated for a predetermined number of stretches (e.g., 6 stretches). During the first week of the patient's treatment, typically one session a day is performed. During the second week, typically two sessions per day are performed. During the third and following weeks, typically three sessions per day are performed.

The above described orthosis devices allow the patient to do these sessions outside of the confines of the doctor's or physical therapist's office. Due to the fact that there are no medically trained personnel to oversee this treatment, the opportunity to stray from the protocol is introduced. In addition, the patient is responsible for the tracking of his or her own progress until reporting back to the physical therapist or doctor. Both of these conditions have the possibility of introducing a high margin of error. Most recently, physicians have expressed an interest in keeping better records of an individual patient's progress during the rehabilitation process. Unfortunately, in many cases, since the rehabilitation process occurs mostly within the confines of the patient's home, it is difficult for a physician to keep an accurate record of the patient's progress.

There are other areas in which patient education and compliance outside the immediate supervision of a health care professional remain problematic. For example, electrical stimulation of bone growth for treatment of fractures requires a regime of therapy that demands patient adherence in order to optimize the stimulatory effects.

Thus, there exists a need for an improved patient monitoring system and method.

SUMMARY OF THE INVENTION

The present invention provides a monitor for use with a device, such as an orthosis device, that detects the type of orthosis device to which the monitor is attached, so that the monitor may access the correct parameters and/or firmware appropriate for the attached orthosis device without the need for such parameters and/or firmware being downloaded to the monitor.

The present invention also provides a monitor for use with an orthosis device that provides assurances the patient is actually wearing the orthosis device during his/her exercise period and is not falsifying usage, such assurances being provided by taking temperature measurements showing that the orthosis device is being properly used.

The present invention also provides a monitor used with an orthosis device having first and second carriage members for rehabilitative stretching by a patient during physical therapy. The monitor takes position measurements of the carriage members to determine if a stretch is being held in accordance with a stretching protocol.

In another embodiment, the monitoring system notifies the patient that the time period for holding a stretch has terminated in accordance with a stretching protocol.

Consistent with the title of this section, the above summary is not intended to be an exhausive discussion of all the features or embodiments of the present invention. A more complete, although not necessarily exhaustive, description of the features and embodiments of the invention are found in the section entitled "Detailed Description Of The Preferred Embodiments".

BRIEF DESCRIPTION OF THE DRAWINGS

A more complete appreciation of the present invention and many of the attendant advantages thereof will be readily obtained as the same becomes better understood by reference to the following detailed description when considered in connection with the accompanying drawings, wherein:

FIG. 4 is a block diagram of the hardware used in the monitor of the present invention when in the treatment mode of operation.

FIG. 5 is a block diagram of the hardware used in the monitor of the present invention when in the data transfer mode of operation.

DETAILED DESCRIPTION OF THE INVENTION

Figure 1:
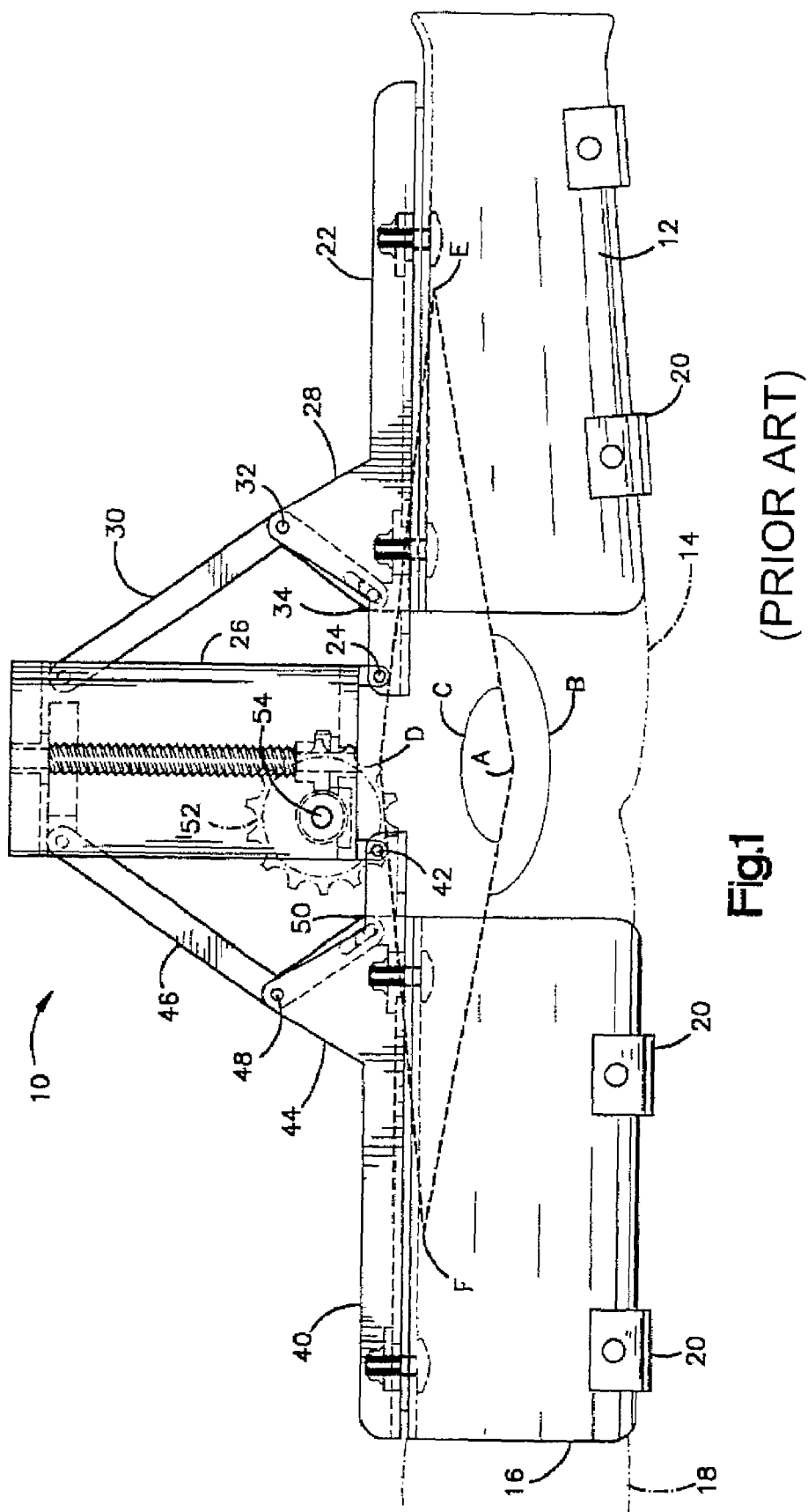
FIG. 1 is a view of an illustrative orthosis device used with the monitor in accordance with the present invention.
Figure 2:
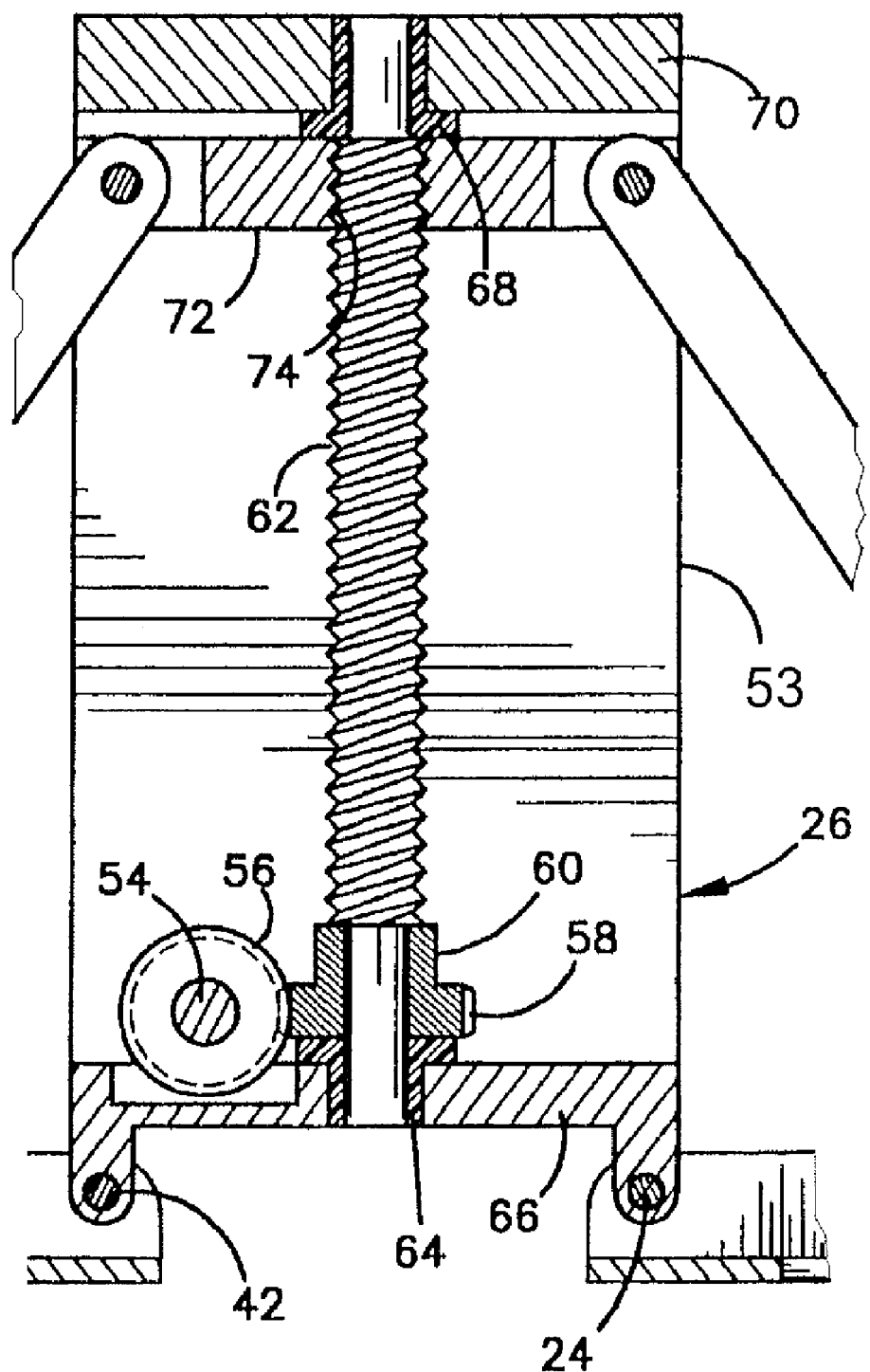
FIG. 2 is an enlarged sectional view of tower of FIG. 1 including the drive mechanism.

Referring to FIGS. 1 and 2, there is illustrated one of many possible prior art orthosis devices, generally indicated by the reference number 10, which may be used with the patient monitor of the present invention. More specifically, this particular illustrative orthosis device 10 is described in U.S. Pat. Nos. 5,395,303; 5,285,303; 5,285,773; 5,213,094; and 5,167,612 to Bonutti, et al., which are incorporated herein.

In FIG. 1 the orthosis device 10 is illustrated as attached to a human arm, for moving the elbow joint which is between the upper arm and the forearm. The orthosis 10 includes a first cuff 12 for attachment to a first body portion 14 such as the forearm, and a second cuff 16 for attachment to a second body portion 18 such as the upper arm. The term "cuff" as used herein means any suitable structure for transmitting the force of the orthosis to the limb portion it engages. The first body portion 14 is joined to the second body portion 18 at the elbow joint designated A. Each of the first and second cuffs 12 and 16 includes a plurality of loop connectors 20 for receiving straps extending around the body portions 14 and 18 to clamp the cuffs 12 and 16 to the body portions 14 and 18. The first cuff 12 is mounted for sliding movement on a first cuff arm 22. The term "cuff arm" as used herein means any suitable structure for transmitting the force of the orthosis to the cuff and thence to the limb portion. The first cuff arm 22 is pivotally mounted by a pin 24 to a tower 26. The first cuff arm 22 includes a support 28. A first lever arm 30 extends from the tower 26 and is pivotally connected to the support 28 by a pin 32. The first lever arm 30 is pivotally connected to a cuff actuator block 34. The cuff actuator block 34 is fixed to the first cuff 12 and is slidable along the first cuff arm 22 in a manner as described below. The second cuff 16 is mounted for sliding movement on a second cuff arm 40. The second cuff arm 40 is pivotally mounted by a pin 42 to the tower 26. The second cuff arm 40 includes a support 44. A second lever arm 46 extends from the tower 26 and is pivotally connected to the support 44 by a pin 48. The second lever arm 46 is pivotally connected to a cuff actuator block 50. The cuff actuator block 50 is fixed to the second cuff 16 and is slidable along the second cuff arm 40 in a manner as described below.

As shown in FIGS. 1 and 2, the tower 26 is a box-like structure including a lower housing 66 and an upper housing 70 joined by a front plate (removed) and a back plate 53. A drive mechanism for the orthosis device 10 is disposed substantially within the tower 26. The drive mechanism includes a manually actuatable knob 52 (FIG. 1) which is fixed to a shaft 54. The shaft 54 extends into the tower 26 and a gear 56 (FIG. 2) is fixed to the shaft. The gear 56 engages external gear teeth 58 on a gear 60. Rotation of the gear 56 about its axis causes rotation of the gear 60 about its axis. The gear 60 is fixed to an externally threaded lead screw 62. One end of the lead screw 62 is journalled for rotation in a bushing 64 mounted in a lower housing 66 of the tower 26. The opposite end of the lead screw 62 is journalled for rotation in a bushing 68 mounted in an upper housing 70 of the tower 26. An arm actuator block or base link 72 has an internally threaded opening 74 though which the lead screw 62 extends in threaded engagement. As the lead screw 62 rotates, the actuator block 72 moves axially along the lead screw 62 within the tower 26. This mechanism provides the "rotating means" for rotating the first cuff arm 22 relative to the second cuff arm 40 and thereby expanding or reducing the angular relationship therebetween.

In operation, the orthosis device 10 of the prior art may provide for distraction of the joint through an entire range of motion. Movement of the cuff arms to extend the joint results in distractive forces being applied to the joint. These distractive forces are limited and controlled by having the cuffs 12 and 16 slidable on the cuff arms 22 and 40, respectively. The cuffs 12 and 16 are selectively moved along the cuff arms 22 and 40, during relative movement of the cuff arms 22 and 40, to provide the proper amount of distractive forces to the joint and to limit compressive forces on the joint. Thus, the orthosis device 10 illustrates one of many orthosis devices that are well suited for stretching therapy.

It should be understood that the orthosis device 10 can be used to extend or flex other joints in the body, such as a knee joint or a wrist joint or ankle joint, with the construction of the orthosis 10 in such case being varied to fit the particular application. A few more illustrative examples are shown in U.S. Pat. No. 6,502,577 for finger joints orthosis, U.S. Pat. No. 6,113,562 for a shoulder orthosis, and U.S. Pat. No. 5,848,979 for a hand orthosis. Moreover, it is contemplated that the monitoring unit of the present invention may also be used for other types of devices, including, but not limited to, rehabilitative devices implementing isometric exercises and those in the continuous passive motion (CPM) area.

To generalize the description of the one class of orthosis devices that may be used with the present invention, such as orthosis devices including (but are not limited to) the stretching orthosis device 10 of FIGS. 1 and 2, isometric orthosis devices, and CPM orthosis devices, the following generic terminology is used in the appended claims. The orthosis devices used with the monitoring system in accordance with the present invention generally are for moving a first portion and a second body portion of a patient connected by a joint. These orthosis devices typically include a first carriage member for receiving the first body portion and a second carriage member for receiving the second body portion. Each carriage member has proximal and distal ends. The second carriage member and the second carriage member are movably connected about their proximal ends so that the first carriage member pivots relative to the second carriage member about an axis intermediate to the first and second carriage members. Hence, the carriage members may move from a first position to a second position and in so doing change the angle defined by the two carriage members.

In the illustrative embodiment of the stretching orthosis shown in FIGS. 1 and 2, the first and second carriage members each include the cuff arm 22 or 40 and a cuff 12 or 16 for connecting cuff arm 22 or 40 to one of said body portions 14, with the cuff 12 or 16 slidably mounted on the cuff arm 22 or 40. In other orthosis devices not directed toward stretching exercises, such those directed toward isometric exercises, the first carriage member and the second carriage member are merely pivotally connected at their proximal ends (frequently adjustably locked in fixed relationship). An example of a simplified orthosis device is shown in U.S. Pat. No. 5,116,296 to Watkins et al. and is incorporated herein by reference thereto. Another example is described in U.S. Pat. No. 5,052,375 to Stark et al. (also incorporated herein by reference thereto), wherein the two carriage members are interconnected by an adjustable hinge and the angle between the respective distal end sections can be adjusted relative to one another. The angular position between the first carriage member and the second carriage member is one of the parameters that is measured by the monitoring system in accordance to be present invention, but as will be discussed hereinafter, the monitoring system includes other sensors for measuring other parameters, such the identification of the orthosis device to eliminate the need for external unit configuration and temperature as an indication the orthosis device is actually being used.

In the case of using the temperature and device identification sensors, the monitoring system of the present invention may be used with any number of different types of orthosis devices. More specifically, any orthosis device needing assurances that the user is actually wearing the orthosis device during his/her exercise period using the orthosis, and not falsifying usage, may make use of the monitoring system of the present invention for temperature measurements which provides evidence that the orthosis is being properly used. Likewise, with monitors using different parameters or firmware for different orthosis devices, the family of orthosis devices may make use of the device type identification sensor, which will allow the monitor to access the correct parameters and/or firmware appropriate for a particular orthosis device without the need for parameters and/or firmware to be downloaded to the monitor.

Figure 3:
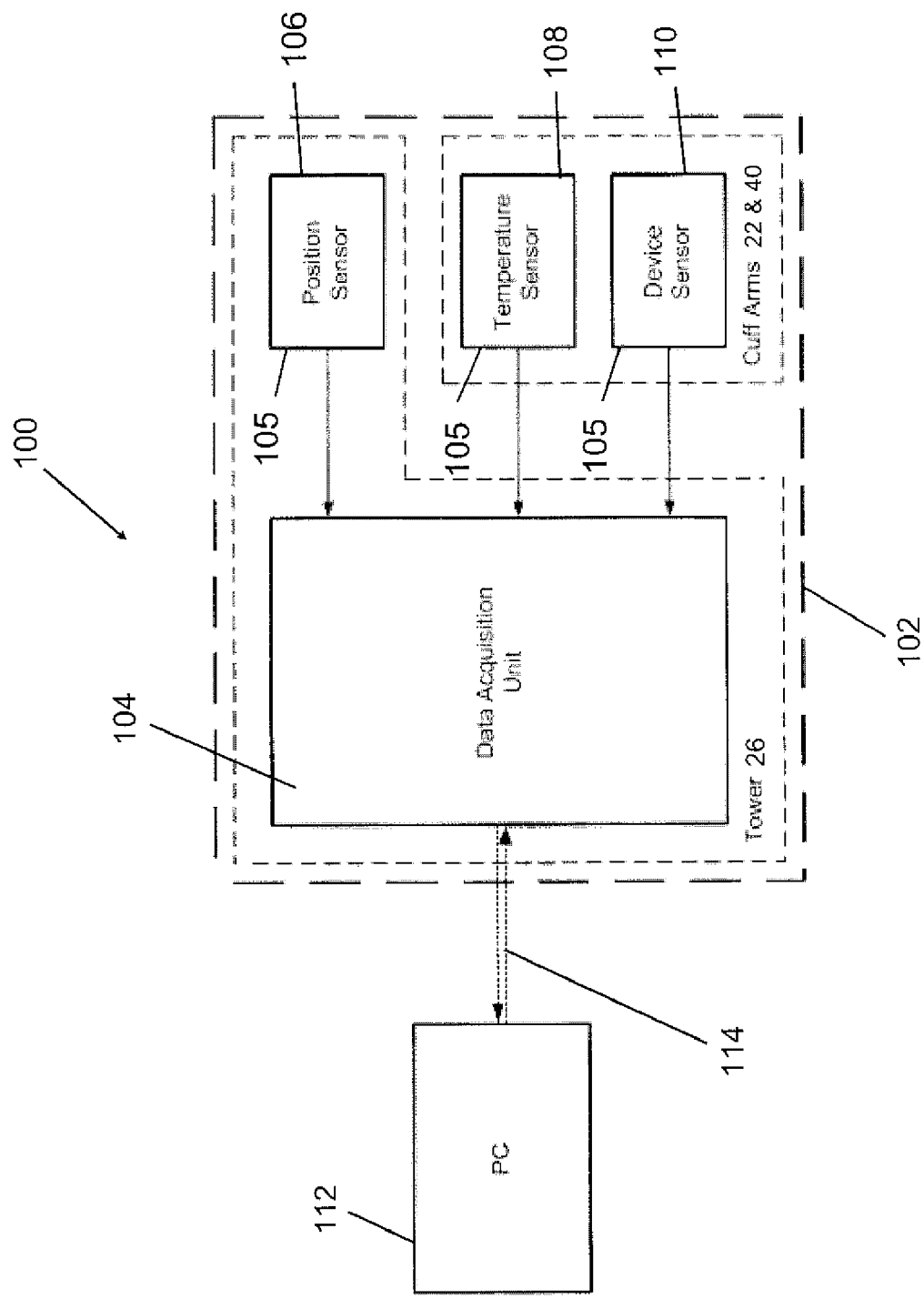
FIG. 3 is a block diagram of the monitoring system in accordance with the present invention.

Referring to the block diagram of FIG. 3, a patient monitoring system 100 for use with a device such as a physical therapy orthosis, like the orthosis device of FIGS. 1 and 2, is shown. The patient monitoring system 100 includes a standalone monitor 102 which can be incorporated into the orthosis device of FIGS. 1 and 2. More specifically, the monitor 102 has a data acquisition unit 104 mounted on the outside of the tower 26 (shown by a dashed line), such tower 26 being described with respect to FIGS. 1 and 2. Additionally, the monitor 102 includes a plurality of sensors 105, three of which are shown in FIG. 3 as a position sensor 106, a temperature sensor 108, and an optional device type sensor 110. As shown by the dashed line, the temperature sensor 102 and the device sensor are mounted on one of the cuff arms 22 and/or 40 shown in FIGS. 1 and 2.

As an overview of the monitoring system 100 when applied to a stretching orthosis such as that shown in FIGS. 1 and 2, a patient is prescribed treatment by a physician or physical therapist, with the prescribed treatment using a given orthosis device having a monitor 102. In a first mode of operation (data transfer or administrative mode), the appropriate orthosis device is modified to fit a patient's specific requirements by the physician or physical therapist downloading the required parameters to the monitor 102. This data transfer mode of operation is used only by the physical therapist or doctor.

In a second mode of operation (treatment mode), the user connects the sensors 105 to the data acquisition unit 104. The monitor 102 controls each exercise session with the patient by stepping the patient through his or her treatment following the previously described stretching protocol. During the critical sections of this treatment in a first mode of operation, the monitor 102 monitors the operation by taking measurements from the sensors 105 and storing them in memory. These retrieval and storage operations are accomplished via a micro-controller and an EEPROM, which will be described in detail hereinafter. Preferably, the unit 104 is able to store approximately two months worth of sessions. Alternatively, the data can be transmitted to another data storage unit. This transmission can occur instantaneously or at set intervals.

At the time of the follow-up appointment with a physician or physical therapist, the user disconnects the unit 104 from the orthosis device and disconnects the sensors 105. Then the user brings the unit 104 to the physician or physical therapist. At this point, the unit 104 again uses the data transfer mode of operation. The information is transferred from the unit 104 to a computer 112 at the office of physician or physical therapist. The memory containing such data in the unit 104 is then erased. This computer 112 uses data analysis software to further manipulate the data and present it for display by the computer 112.

Overviews of the hardware of the data acquisition unit 104, as configured in the above-described modes of operation, are provided in FIGS. 4 and 5. In both FIGS. 4 and 5, a microprocessor 120 (PIC16F877) uses an external memory 122 and is electrically coupled to a display device 124, in the form of a parallel LCD. FIG. 4 shows the hardware configured for the treatment mode, wherein the microcontroller 120 is electrically coupled to the sensors 105 via buses 126 and 128. FIG. 5 shows the hardware configured in the data transfer mode to be in communication with the computer 112 via a cable 130 coupled to an RS-232 port 132 on the monitor 102. The MAX 233, shown by reference numeral 133, is a Maxim MAX233a device which is used to convert the serial communication voltages used on the microprocessor 120 to the RS-232 levels required by the computer 112.

With reference to FIGS. 3, 4 and 5, the two modes of operation of the monitor 102 will be described in detail, with the mode of operation being set by the computer 112 via the cable 114. The data transfer mode is entered when the monitor 102 is turned on with the monitor-to-PC cable 114 being inserted into the data acquisition unit interface provided by the port 116 of the monitor 102. As described above, this mode is used for the configuration of the monitor 112 as well as the retrieval of the acquired data after the monitor is returned by the patient. Through device configuration by the computer 112, various options may be set allowing the monitor 102 not only to be used with the illustrative orthosis device of FIGS. 1 and 2, but also to be used with the entire family of rehabilitation devices without modifying the hardware or firmware of the data acquisition unit 104. The device configuration options are stored on various orthosis devices in the memory 122. The communications protocol for configuring the monitor 102 is provided below in TABLE I:

TABLE I

| Command | Name | Expected Arguments | Description |
|---|---|---|---|
| 0x00 | Send data | none | Sends the patient data to the PC via the RS-232 port. |
| 0x11 | Set reps | number of reps (ASCII) | Set the number of stretches the patient performs per session. |
| 0x22 | Set mins | number of minutes (ASCII) | Set the number of minutes the patient will hold each stretch. |
| 0x33 | Set secs | number of seconds (ASCII) | Set the 10's position of the number of seconds to hold each stretch. |
| 0x44 | Set ID | device id | Sets the device ID. The first time monitor is restarted & connected to orthosis device after setting the device ID, the user will be prompted to configure the device. |
| 0x55 | Set clock | minutes (BCD) hours (BCD) date (BCD) month (BCD) | Sets and configures the real time clock with the given arguments. |

TABLE I-continued

| Command | Name | Expected Arguments | Description |
|---|---|---|---|
| 0x66 | Set mask | comparison mask | Sets the mask used to compare measurements for position sensor. This is used to compensate for noisy sensors. |
| 0xFF | Delete | none | Marks all data as deleted from the EEPROM storage. |

It should be noted, that with the above protocol, the device id (identification) is set by the computer 112. In this embodiment, the device type sensor 110 shown in FIG. 3 is not used. Optionally, the device type sensor 110 may be used, in which case the "id" command is not needed. The alternative embodiment using the device type sensor 110 is described hereinafter.

The treatment mode is used when connected to the sensor 105 through the data acquisition unit interface 132. The sensor hardware unit contains all the necessary circuitry for the operation of the current sensors 105 as well as power and ground for the expansion ports. Referring back to FIGS. 1, 2 and 3, the temperature sensor 108 is embedded into one of the cuffs 22 or 40 of the orthosis device 10. The temperature sensor 108 is not necessarily intended for an accurate measurement of the patient's body temperature while using the orthosis device 10, but is a way to ensure that the patient is actually wearing the orthosis device 10 during the treatment session.

Figure 6:
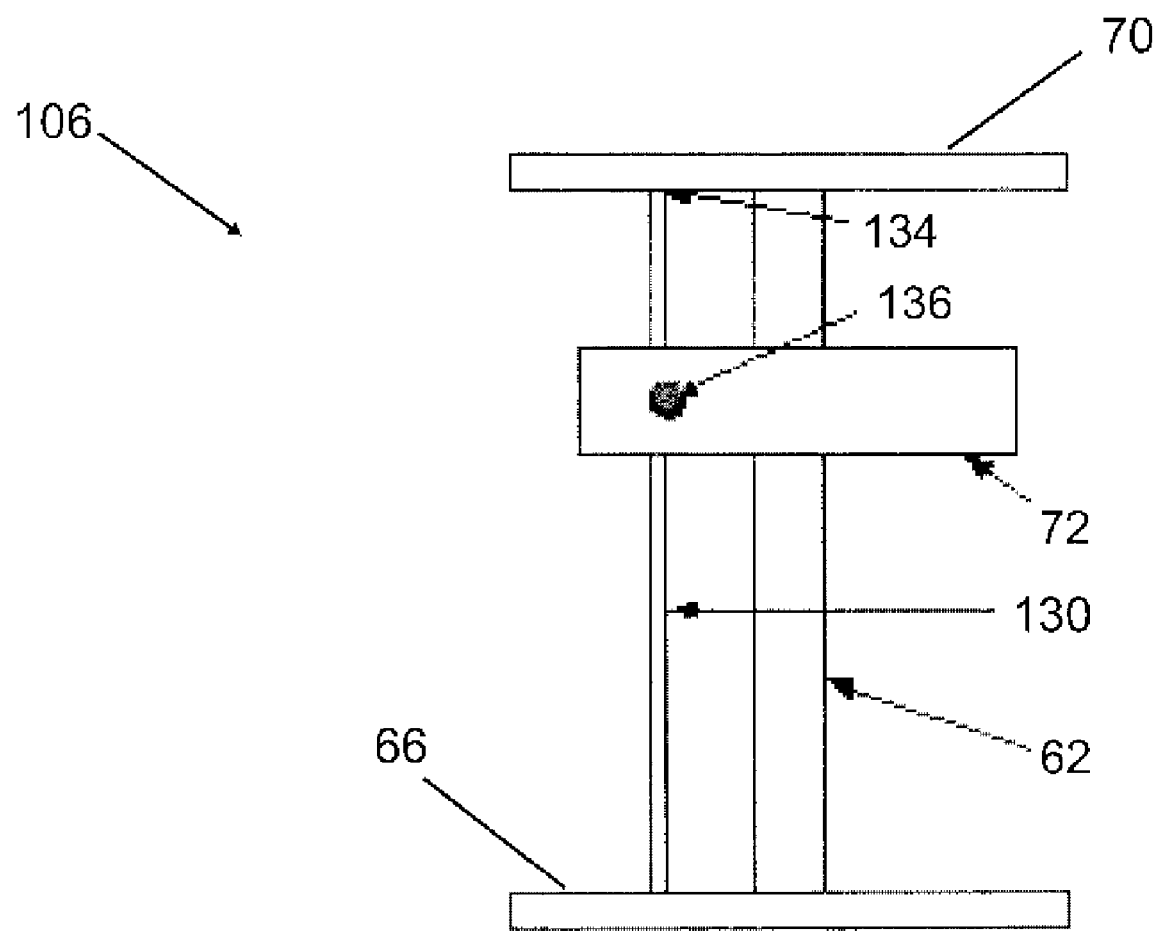
FIG. 6 is a schematic diagram of the position sensor used in the present invention.

Modifications to the tower 26 shown in FIG. 2 to include the position sensor 106 of FIG. 3 are shown in the schematic diagram of FIG. 6. Referring to FIG. 6, the overall structure remains the same as shown by the lead screw 62, lower housing 66, actuator block 74, and upper housing 70. What is added is a spring 130 which extends from the lower housing 66 to the upper housing 70 and is disposed in parallel relationship with the lead screw 62. The spring 130 passes through an aperture 132 in the actuator block 74. An electrical contact 134 is embedded in the upper housing 70 and is in electrical contact with an upper end of the spring 130. A second electrical contact 136 is embedded in the actuator block 74 and is in electrical engagement with the spring as it slidingly passes through the aperture 132 when the actuator block 74 is moved along the lead screw 62, such movement being caused by the rotation of the lead screw, as discussed with respect to FIGS. 1 and 2. More specifically, referring back to FIGS. 1 and 2, in addition to FIG. 6, the rotation of the lead screw 62 is used to drive the device cuffs 22 and 40. As the knob 52 on the exterior of the tower 26 is turned, the actuator driver 72 moves up and down accordingly, thus moving the cuffs 22 and 40. By placing the contact 136 on the actuator driver 72 and one at the top of the spring, a variable resistor is created. This variable resistor is then used in a voltage divider circuit (shown hereinafter) to create a center-tapped potentiometer to monitor the angle formed by the arms 22 and 40 during the treatment.

Referring to FIGS. 3–5, the first time that the hardware sensors 105 are attached after the device identification number has been set during the above described data transfer mode, the user will be prompted to extend the orthosis device 10 to the maximum and then the minimum position to calibrate the device 10. These measurements are then stored in the memory 122 for use during the remainder of the treatment sessions to calculate the angle between the arms of the device 10.

Figure 7:
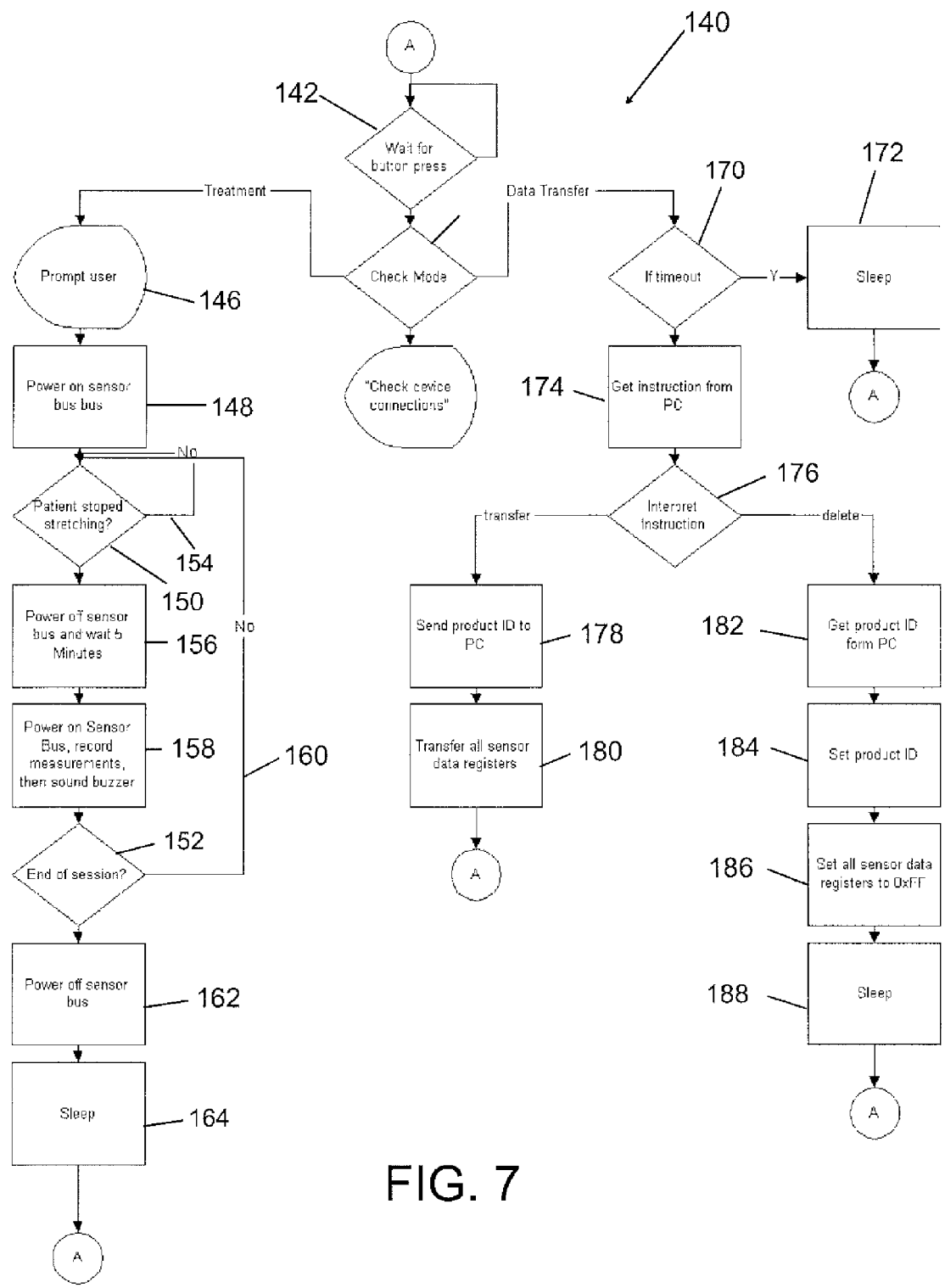
FIG. 7 is a flow chart of the firmware embedded in the monitor of the present invention.

Referring to FIG. 7, both the treatment mode of operation and the data transfer mode of operation for the monitor 102 are described in a flow chart of a firmware program 140, which is embedded in the data acquisition unit 104. At step 142, the firmware program 140 waits until a button is pushed by the physician or physical therapist specifying the selected mode of operation. At step 142, the mode is checked, and if the user selected the treatment mode, the program 140 branches to the "Treatment" branch. If the user selects the data transfer mode of operation, then the program 140 branches to the "Data Transfer" branch.

After the patient/user begins his or her treatment session, the monitor 102 has already been set for the treatment mode of operation. First, a splash screen is displayed with the name and version of the firmware included in the data acquisition unit 104. The session runs according to the following flow chart shown in FIG. 7, as shown on the left side. At step 146, the user is prompted to turn the knob 52 (see FIG. 1) until a gentle stretch is felt. At step 146, the program checks to see if there is power on the sensor bus. If yes, the program goes to step 150 and if no, the program branches to step 152. The micro-controller 120 at step 150 begins taking measurements of the position sensor 106 in the tower 26 (see FIG. 3) to see if the patient has stopped stretching. The micro-controller 120 (see FIG. 3) continues in a loop 154 until the current position measurement of the position sensor 106 matches the last one, which indicates that the patient has stopped stretching. More specifically, the user definable mask, set via the RS-232 port in data transfer mode, is used to compensate for noisy sensors 106, and the natural variation in analog to digital conversion. When the two position measurements of the position sensor 106 match, it is assumed that the user of the orthosis device 10 has stopped turning the knob 52 and is ready to hold the stretch. The position sensor 106 of FIG. 6, in combination with execution of this firmware routine, provides the "position sensor means" for detecting when there is a stop in movement of the first arm cuff 22 relative to the second arm cuff 40 when a patient starts to hold a stretch.

Upon the program determining that the patient has started to hold a stretch, the program proceeds to step 156, where the power is turned off on the sensor bus and the program waits a preset amount of time, e.g., 5 minutes. As specified in the previously described stretching protocol, the user is to hold the stretch for 5 minutes and the time is displayed on the LCD 124 (see FIG. 3). As shown in Table I above, the time to hold a stretch is also configured in the data transfer mode, which allows for easy modifications of this protocol if needed. This firmware routine provides "timing means" for generating a patient detectable signal aster the expiration of the predetermined time period, with in this illustrative example, is 5 minutes.

Upon completion of the hold for the stretch, the program 140 proceeds to step 158, where power is turned on to the sensor bus, all measurements of the sensors are recorded and a sound buzzer is triggered to indicate the end of the period for holding the stretch. More specifically, all of the analog conversions of the sensor 106 are repeated and stored into the memory 122. When all the measurements are saved, a 16 bit address pointer for the memory 122 is updated in the micro-controller. If the user interrupts a stretch before it is completed, then that session will automatically be overwritten by the next session without the need for more complicated error checking. At step 152, if the number of stretches is less then the amount defined by the treatment protocol, the stretch loop is repeated via loop 160. If the number of stretches completed is equal to the amount defined by the treatment protocol at step 152, then a session complete prompt is displayed on the LCD 124 and the program 140 proceeds to step 162, where the power is turned off and then the program goes to sleep at step 164.

Referring to the right side of the flow chart in FIG. 7, the data transfer mode of operation is shown. As previously described with respect to FIG. 5, the data acquisition unit 104 is in communications with the computer 112. First, the physician or physical therapist would have selected this mode of operation and the program would recognizes the same at step 144 and taken the "Data transfer" branch to step 170. If there is a timeout, the program 140 proceeds to a sleep state at step 172. If there is no timeout, then the program proceeds to step 174, where the micro-controller of 120 (FIG. 5) fetches an instruction from the computer 112. The instructions from the computer 112 include, but are not limited to, the commands listed in TABLE I above. The micro-controller 120 interprets the instruction at step 176. Depending upon the instruction, the program takes the "transfer" branch or the "delete" branch.

When the program 140 takes the "transfer" branch, at step 178, the program sends the product ID to the computer 112. Then at step 180, all the sensor data is transferred from the memory 122 to the computer 112. When the program 140 takes the "delete branch", at step 182, the program 140 obtains from the computer 122 the product ID (see TABLE I above), then sets the product ID at step 184 and erases the existing sensor data by setting all sensor data to 0xFF (see TABLE I above). Then the program 140 proceeds to its sleep state at step 188. With this embodiment, it should be clear that the device sensor 110 is not included, because the computer 112 sets the device ID.

Figure 8:
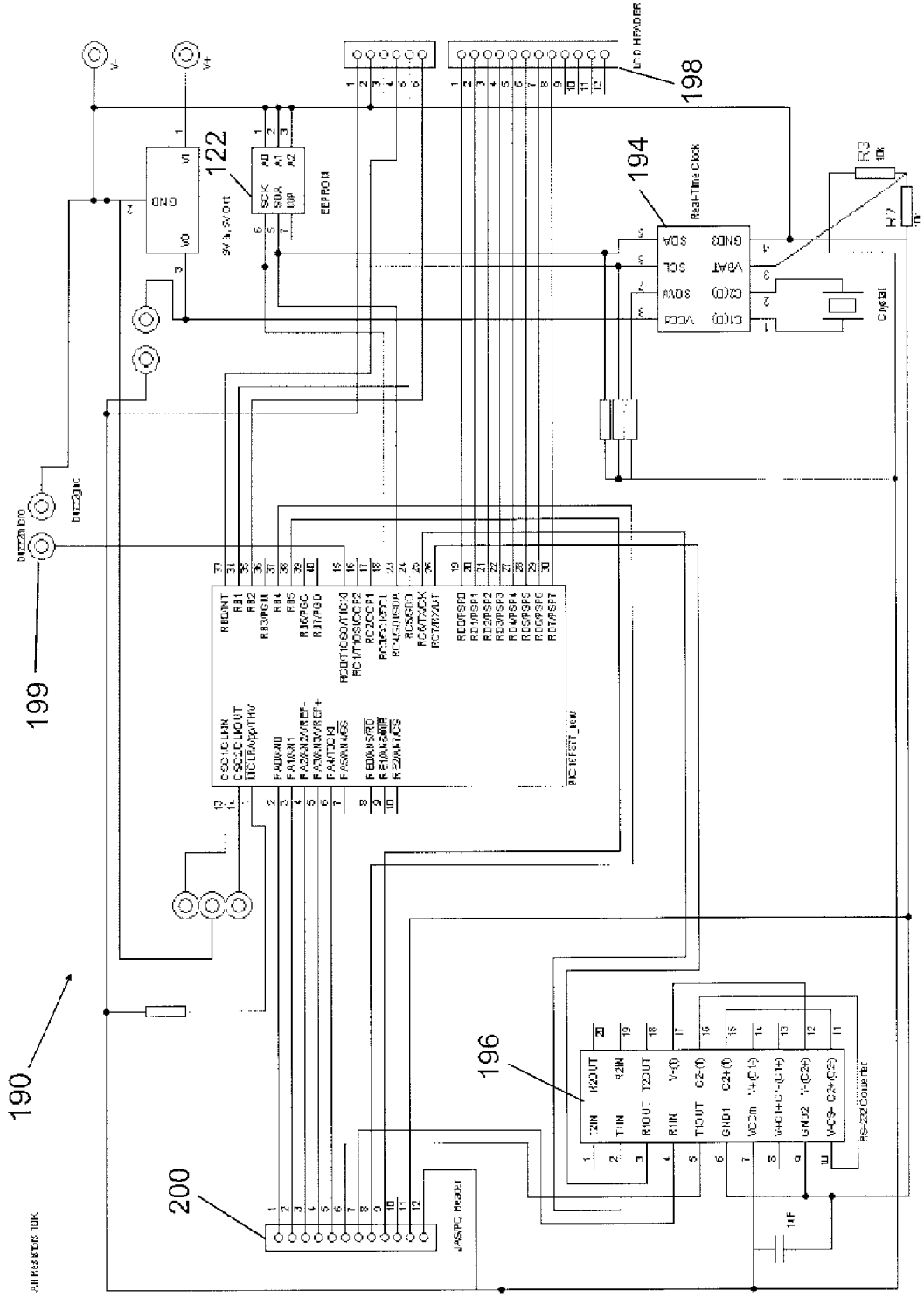
FIG. 8 is a detailed schematic of the hardware used in the monitor of the present invention.

In FIG. 8 a detailed schematic 190 of the hardware for the data acquisition unit 104 of FIG. 3 is shown, with such hardware having been generally described on a higher level in FIGS. 4 and 5. Referring to FIG. 8, the micro-controller 120 preferably comprises a Microchip PIC16F877 micro-controller. This PIC16F877 micro-controller is a 40 pin, 8 bit CMOS Flash microcontroller configured using the following pin assignments in TABLE II below:

TABLE II

| | Name | Direction/Mode | Port |
|---|---|---|---|
| 1 | Temp | Analog | RA0 |
| 2 | Position | Analog | RA1 |
| 3 | Expand 1 | Analog | RA2 |
| 4 | Expand 2 | Analog | RA3 |
| 5 | Expand 3 | Analog | RA4 |
| 6 | LCD RS | Out | RB0 |
| 7 | LCD R/W | Out | RB1 |
| 8 | LCD E | Out | RB2 |
| 10 | Mode 1 | In | RB4 |
| 11 | Mode 2 | In | RB5 |
| 14 | Buzzer | Out | RC0 |
| 16 | SCL | I2C | RC3 |
| 17 | SDA | I2C | RC4 |
| 18 | Serial Tx | USART | RC6 |
| 19 | Serial Rx | USART | RC7 |
| 20 | LCD DB0 | Out | RD0 |
| 21 | LCD DB1 | Out | RD1 |
| 22 | LCD DB2 | Out | RD2 |
| 23 | LCD DB3 | Out | RD3 |
| 24 | LCD DB4 | Out | RD4 |
| 25 | LCD DB5 | Out | RD5 |
| 26 | LCD DB6 | Out | RD6 |
| 27 | LCD DB7 | Out | RD7 |

The external memory 122 is a Microchip 24AA64 I2C EEPROM. The memory 122 is connected to the controller 120 via the I2C serial communications bus 192. The memory 122 has 64K bits of EEPROM and is used for the storage of the patient data. The operation of this device is limited to the low speed bus operation due to the use of a 4 MHz crystal. The LED 124 is a Hitachi 44780 compatible LCD operating in 8 bit parallel mode. The Hitachi LCD is an industry standard, and was chosen because any 14×2 LCD could then easily be substituted. A Dallas Semiconductor DS1307 I2C real time clock 194 is provided, which is connected to the I2C bus 192 along with the EEPROM memory 122. This clock 194 is used to record, to the nearest hour, when the actual stretch sessions were performed. This allows the PC software for the computer 112 (see FIG. 3) to group the stretches into sessions.

This micro-controller 120 has an onboard port capable of 8-channel analog to digital conversion at 10-bit resolution making it a powerful tool in data acquisition. The controller 120 also supports both SCI and I$^2$C serial communication. The SCI module of the controller 120 is used to communicate with the computer 112 through standard RS-232 port of a RS-232 communications interface 196. This communications, for example, allows for further analysis of the data by the physical therapist or doctor. The I$^2$C protocol will used to interface with the memory 122 and the real time clock 194. The use of external memory 122 will be needed as the 128 bytes of EEPROM storage for the internal memory of the controller 120 is insufficient to store the data acquired from the sensors. The controller 120 is electrically coupled to a Piezo buzzer (not shown) via the pin RC0 being connected to the terminal 199.

Figure 9:
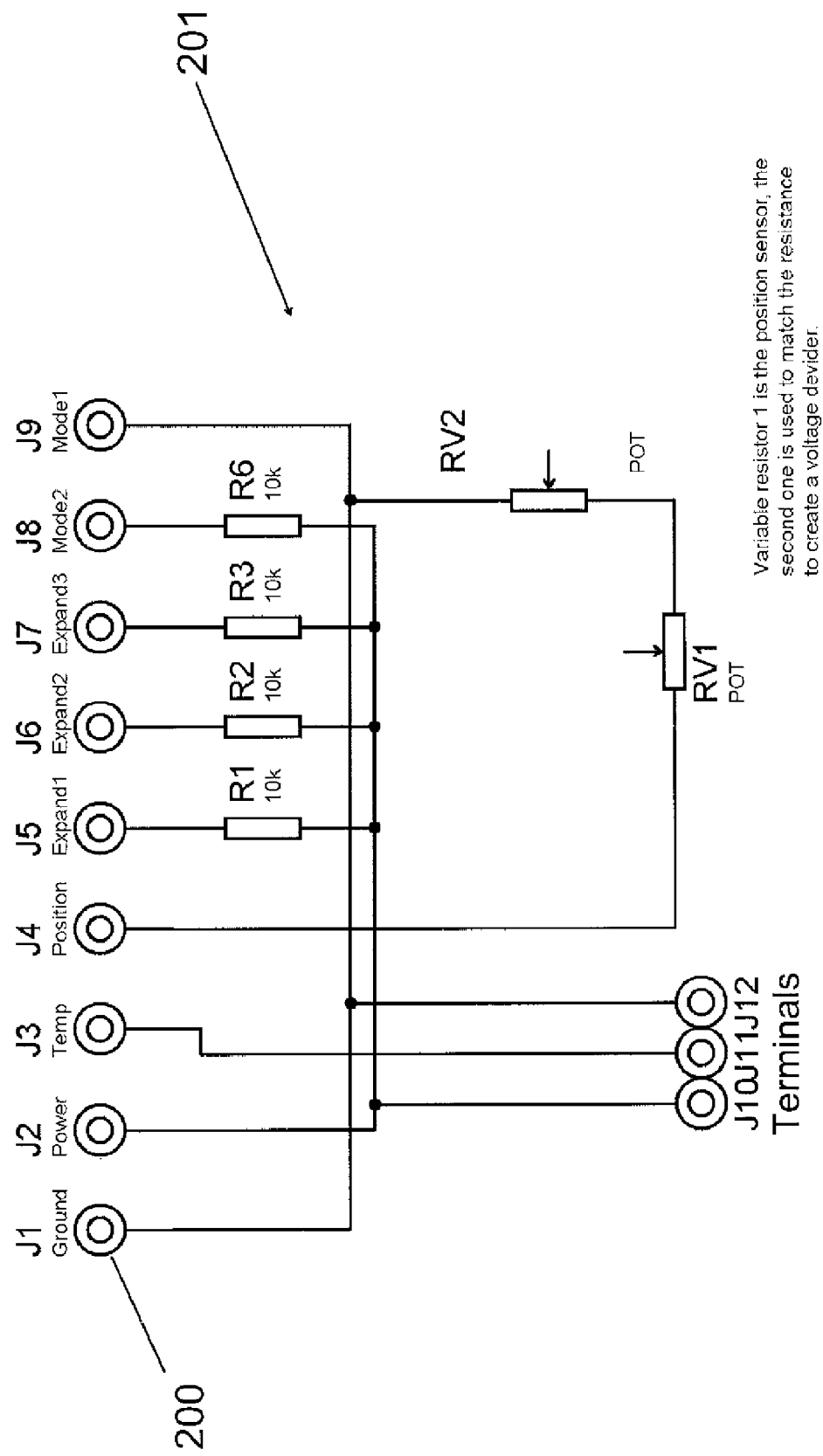
FIG. 9 is a schematic of the circuitry for the sensors used in the monitor of the present invention.

In FIG. 8, there is also shown the header 198 (including insulated terminals or leads) for connecting the LCD 124 of FIGS. 4 and 5. Also, there is shown a header 200 for connecting with the sensors (terminals J3–J6) and the computer 112 (for selecting the mode of operation via terminals J8 and J9). The sensor hardware schematic 210, including the header 200, is shown in FIG. 9 in more detail. Referring to FIG. 9, the terminals J1–J12 of header 200 are electrically coupled to the ports of the controller 120 as specified in TABLE II. A first variable resistor RV1 comprises the resistance of the position sensor 106 (FIG. 3) and a second variable resistor RV2 is used to match the resistance to create a voltage divider as previously described, to form a potentiometer, used with the position sensor 106 (FIG. 3).

In an alternative embodiment of the sensor hardware of FIG. 9, it is contemplated that the expansion terminals J5–J7 may be used for additional sensors, including blood pressure, heart rate, and stress indicators. To accomplish this, the sensor bus is modified to use both 3.3 and 5.0 volt supply lines to allow for the plug-in of multiple expansion sensors. With a selectable supply voltage, a universal connector is provided for both patient data acquisition in the treatment mode and for data transmission to the doctor's office in the data transmission mode selected by cable.

Referring to FIG. 3, the temperature sensor 108 is a Dallas Semiconductor LM34DZ temperature sensor. This temperature sensor was not used to measure the patient's actual temperature but was used to confirm that the patient was actually using the device.

With reference to FIG. 3, the patient monitoring system software running on the computer 112 briefly will be described. The software application provides a therapist a way of obtaining the data stored on the data acquisition unit 104 and presents it in a meaningful way. One function of the Patient Monitoring System software is the ability to view patient records. The system checks to ensure that all fields are entered and informs the user if one or more of the fields are blank. In addition, the system checks the patient name entered against the array of current patient names. If the entered name is invalid, the system reports no patient found. Otherwise, the system uses the "Patient ID" field from the array to access the data file for that particular patient. This file contains all of the information obtained from the data acquisition unit (FIG. 3) from previous visits. The system then displays the contents of the file in the grid at the bottom of the form. The grid is another built-in control of Visual Basic 6.0 called the "Microsoft FlexGrid Control 6.0". In addition, the system displays other patient information such as the name of that patient's physician and the date that patient received their orthosis device.

Another function provided by the system software is the form for actually acquiring data from the data acquisition unit 104 (FIG. 3). The screen layout is very similar to that of the form for viewing patient records that are already stored in the system. This form also uses a grid to display the data once it has been obtained from the Data Acquisition Unit. In order to facilitate reading from a communications port, Visual Basic has a control entitled "Microsoft Comm Control 6.0". This control allows communication between the personal computer 112 (FIG. 3) and any device attached to a designated communications port. The user also has the option to change what communications port the system will look for the data acquisition unit on in case other communications ports are already in use by that individual's computer. By default, this is set to COM1.

When the user clicks on the "Acquire" command button, as in other forms, the system checks to see first if all proper text fields have been filled in, and then if the patient name entered is valid. Also, it informs the user to make sure that the data acquisition unit is securely connected to the selected communication port. Next, the system sends out a zero byte on the communication port, which informs the data acquisition unit to begin sending data. The patient monitoring system software then reads in the raw data from the unit, one byte at a time, and stores it into a temporary file called "output.dat". After the data acquisition unit has completed sending all of its data, the system software sends out a byte equal to 0xFF in hexadecimal to inform the data acquisition unit to wipe out its memory and the serial communication is complete.

The next major task that the software application does involves manipulating data. This includes converting the raw data obtained from the data acquisition unit into meaningful values, saving them in the proper patient's file, and displaying them in the grid for the user to examine. First, the system goes through and converts all of the data received from the data acquisition unit into actual integers, instead of the binary form that they are initially sent in. The first major changing of any data occurs with the data representing the time and the date. Actually, the date is composed of a byte representing the month, and one representing the day. The data acquisition unit transmits all three of these values: month, day, and hour, in BCD form (see TABLE I). To do this, the system subtracts a factor of six from the data based on the value of its upper four bits. For example, the BCD value of thirty-one is stored in binary as 0011 0001. The system will subtract eighteen (six times the value of the upper four bits, three) from the integer value of the number, forty-nine, to produce the correct result of thirty-one.

The next major conversion occurs with the "Position" readings taken by the position sensor 106 (FIG. 3) and transmitted from the data acquisition unit 104. The data acquisition unit transmits values called Stretch_Min and Stretch_Max during its serial communication with the patient monitoring software. The difference between these two numbers is computed and adjusted to fit a scale of based on the particular device. For example, one orthosis devices allows a range of motion from one hundred thirty-eight to negative ten degrees. Next, each "Position" value is then adjusted accordingly to fit within these two values. In reality, this conversion may not be exactly linear, but since the position sensor need not be as highly accurate as other more expensive models, assuming linearity in this case is acceptable.

The final conversion that the system makes involves the readings from the temperature sensor 108 (see FIG. 3). Based on the specifications of the temperature sensor itself, the voltage increases ten milivolts per degree. The system then fits the binary data into the range of acceptable values. For the most part, the temperature data should be relatively constant. Its primary purpose is to ensure that the patient is actually wearing the device while using it, instead of simply turning it on to take false readings. As a result, the therapist would be able to tell if a reading was false by seeing if any of the temperature values were conspicuously above or below any realistic, expected values. This helps to ensure proper adherence to the stretching protocol.

Figure 10:
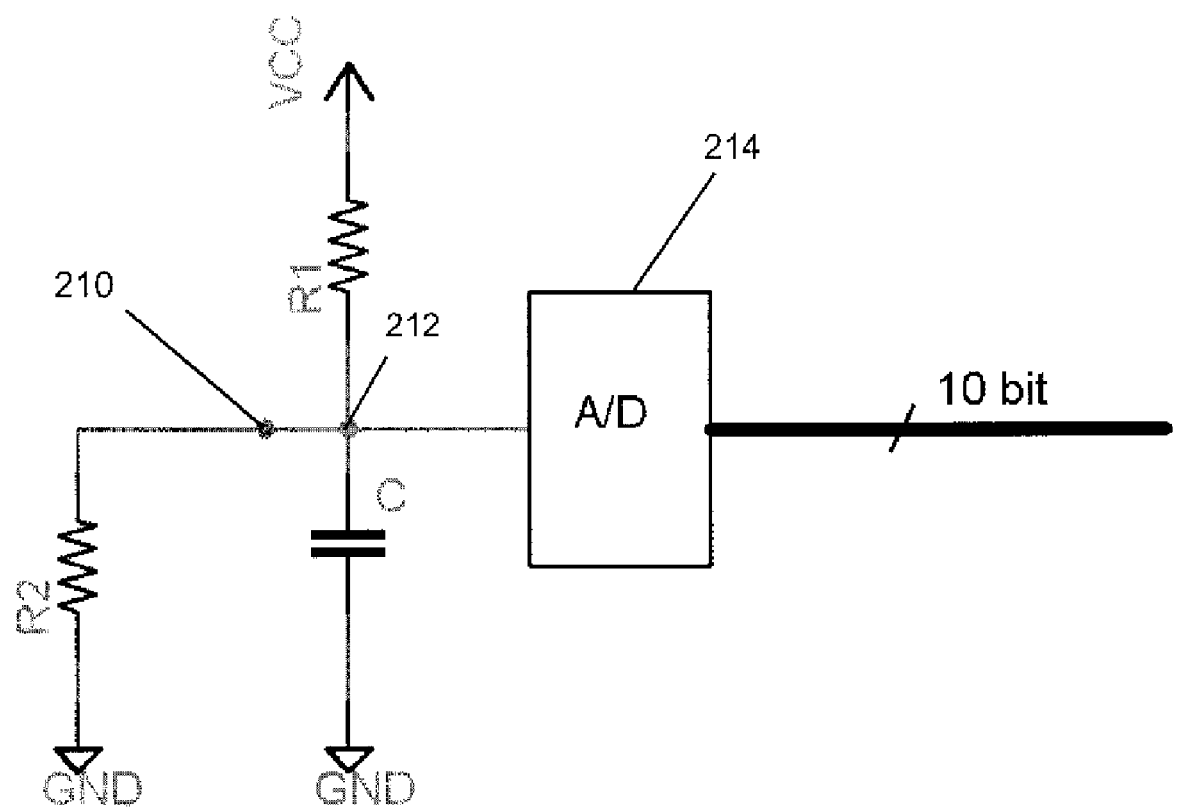
FIG. 10 shows circuit diagram of an alternative embodiment of the monitor which includes a device type sensor in accordance with another aspect of the present invention.

In FIG. 10 an alternative embodiment of the monitoring system 100 shown in FIG. 3 is shown. In this alternative embodiment, the device type sensor 110 shown in FIG. 3 is used. Although shown in FIG. 3, the sensor 110 was not used in the first embodiment, in that the device ID was downloaded by the application software operating on the computer 112 to the data acquisition unit 104. But in this alternative embodiment, the device ID is obtained via the sensor 110. Referring to FIG. 10, each orthosis device is given its own unique resistor R2. Typically, this resistor is mounted on orthosis separate from the data acquisition unit 104, so that the data acquisition unit 104 is not device specific. In the case of the orthosis 10, the resistor R2 enclosed in a protective casing and the casing is mounted to one of the arms 22 or 40. The resistor R2 is electrically coupled on one side to a lead 210 extending from the casing and is electrically coupled at its other side to ground. The lead 210 is connected to the first expansion terminal J5 shown in FIG. 9. The device sensor 110 includes additional circuitry located within the data acquisition unit 104. This additional circuitry includes a node 212, a capacitor C (having a value of 0.1 uF) electrically coupled between the node 212 and electrical ground, a resistor R1 electrically coupled between the node 212 and a voltage source Vcc and a 10 bit Analog-to-digital converter (ADC) 214 connected to node 212.

When the node 212 is electrically coupled to the lead 210 of the resistor R2, the resistor R2 and C are in parallel. The voltage $V_{ADC}$ applied to the ADC 214 is as follows:

$$VADC = \left(\frac{R2}{R2 + R1}\right)(Vcc)$$

In this case the following conditions apply: no cable resistance, so that when R2=infinity, $V_{ADC}$=Vcc; for the PC link cable, when resistor R2=0, then $V_{ADC}$=0 and that there is a valid orthosis device with an embedded resister R2. In this case, the resolution of this device sensor 110 at Vcc=5V would be $2^{10}$=1024, so that 5/1024=5 mV. The following TABLE III provides illustrative values used to identify different orthosis devices (R2 is provided in kilo ohms, $V_{ADC}$ and Range are provided in volts, and R1=10 kilo ohms):

TABLE III

| Device - R2 | $V_{ADC}$ | Range |
|---|---|---|
| 440 | 4.89 | 4.85–4.91 |
| 150 | 4.76 | 4.7–4.82 |
| 100 | 4.54 | 4.45–4.65 |
| 50 | 4.17 | 4.09–4.35 |
| 32 | 3.8 | 3.61–4.06 |
| 18 | 3.21 | 2.96–3.54 |
| 10 | 2.5 | 2.23–2.95 |
| 5.8 | 1.83 | 1.59–2.2 |
| 3.3 | 1.24 | 1.05–1.55 |
| 1.8 | 0.96 | 0.63–1.0 |
| 1.0 | 0.45 | 0.37–0.6 |
| 0.5 | 0.238 | 0.195–0.55 |
| 0.28 | 0.136 | 0.110–0.18 |

As discussed above, this alternative embodiment is utilizable where it is desirable to identify a given orthosis device out of a plurality of possible orthosis devices so as to eliminate the need for downloading parameters, commands and/or firmware for that specific orthosis device. In other words, like the use of the temperature sensor, the orthosis devices making use of this embodiment of the monitor 100 do not need to be directed toward those implementing stretching exercises.

An additional feature that may be added to the Patient Monitoring System software is a "non-programmers" interface wherein a Microsoft® Windows based graphical user interface (GUI) is provided with a plurality of predetermined unit configurations for the monitor system 100 of FIG. 3 are provided in a first window. The user is able to select one of these unit configurations by clicking on the same and dragging the same to a selection window. This feature allows for unit configuration by a therapist or family configuration by an Original Equipment Manufacturer (OEM) without the need for factory assistance. Additionally, a third window may be provided wherein the user may select other system or user variables, by once again dragging the same from the third window to the selection window.

Referring to FIG. 3, aspects of the monitor system 100, such as the device type detector 100 (FIG. 3), may be used with devices other than the stretching orthosis shown by the illustrative embodiment of FIG. 6. Other possible applications for these aspects would be to other types of orthosis devices, such as isometric orthosis devices. Via software, the monitor system 100 may be configured to work with any rehabilitation device having position measurements. The monitor also has the ability to accept other sensor inputs not accounted for previously. The firmware and hardware of the monitor system 100 already provides for the possibility of up to 5 sensor inputs, thus only minor changes in the PC software are necessary in order to view data output from other sensor inputs, such as mentioned with respect to FIG. 9.

After thorough testing of the data transfer capabilities of the monitor 102, it has been concluded that a higher crystal frequency may be more suitable for transmitting the required data over the RS-232 port. Operating the micro-controller at 20 MHz would significantly decrease the data transfer time and would not add much to the cost of the product, but allow the I2C bus to operate in high speed mode as well as allow a higher baud rate for the RS-232 communications.

Having a spring measure the amount of extension/flexion may be a very cost-effective solution for the position sensor 106 of FIG. 6; however, those skilled in the art will recognize that more accurate position sensors may be used.

While various values, scalar and otherwise, may be disclosed herein, it is to be understood that these are not exact values, but rather to be interpreted as "about" such values, Further, the use of a modifier such as "about" or "approximately" in this specification with respect to any value is not to imply that the absence of such a modifier with respect to another value indicated the latter to be exact.

Changes and modifications can be made by those skilled in the art to the embodiments as disclosed herein and such examples, illustrations, and theories are for explanatory purposes and are not intended to limit the scope of the claims. For example, one embodiment of the invention has been described as utilizing cables to transfer data. In this regard, the data transfer can be implemented using fiber optics, a phone line, a cellular phone link, an RF link, and/or other communications channels. Thus, the present invention also envisions the use of wireless means for data transfer. Such wireless means could use technology like the CENTRINO mobile technology and personal digital assistants (PDA's).

Furthermore, the invention has been described as being used by patients and health care professionals. However, limited access to the system and/or data by others could be allowed if authorized by the patient and/or health care professional. On such scenario in which limited access could be granted would be for proof of assurance to an insurance company for a worker's compensation carrier. Others may also have a need to have some assurance that a patient is indeed following through with a compliance protocol.

Although the monitoring system and method have been described primarily in the context of an orthosis device, other applications are contemplated by the present invention. These include other aspects of physical therapy; electrostimulation; bone growth stimulation; drug delivery systems; cardiac rehabilitation; generalized rehabilitation, including compliance; implantable pumps, such as insulin pumps for diabetics; intravenous or implantable pump medication; and implantable or wearable chemical sensors to monitor various physiological parameters such as blood coagulation, blood profile, and blood enzyme content.

For example, in known pharmaceutical delivery systems, a rotatable wheel has a number of compartments, each containing an incremental dose of medications. As programmed, a door opens at a prescribed time and the pill either by weight or by size would be opened up for patient access.

With the present invention, we can externally monitor these drug deliveries systems or internally monitor them. The delivery systems could be used with an implantable pump or implantable blood chemistry sensor. A wireless readout from the pump or sensor could attach, for example, to a wrist watch which would monitor the compliance through a digital readout. A patient could monitor their own blood chemistries or response to particular medications and then these results would be broadcast to physician, extended care, nurse practitioner, nurse, insurance carrier, etc. This would then monitor the changes to a specific drug and then monitor the serum chemistries, for example, blood sugar, etc. These are monitored and then the patient can be monitored through a wireless format to see how they respond to certain medications and have an instant readout through this chemistry monitor without actually having the patient in the office or in the hospital. If the response is not as desired, the delivery protocol can be remotely changed based on the measurements.

In light of the foregoing, it should be understood that while various descriptions of the present invention are described above, the various features could be used singly or in any combination thereof. Therefore, this invention is not to be limited to only the specifically preferred embodiments depicted herein.

Further, it should be understood that variations and modifications within the spirit and scope of the invention might occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A physical therapy apparatus comprising:
    an orthosis device including a first carriage member, a second carriage member pivotally connected to the first carriage member, a control assembly operably connected to the first and second carriage members such that an operation of the control assembly rotates the first carriage member with respect to the second carriage member about an axis intermediate to the first and second carriage members, and an electrical identification;
    a monitor system including a memory having a plurality of control programs for directing operation of different orthodic devices stored therein and for storing patient use data, and a micro-controller being operable for executing at least one of the control programs and for monitoring use of the orthosis device by a patient, wherein the micro-controller utilizes the electrical identification to identify the orthosis device and select the at least one control program; and
    a plurality of sensors operable connected to the monitoring system and including device sensors, for monitoring the orthosis device, and patient sensors, for monitoring a patient,
    a computer having applications software for processing patient use data from the memory, wherein the monitoring system includes a data communications interface to electrically coupled to the micro-controller and the memory to the computer,
    wherein the monitor system is operable between a first mode, data transfer mode, and a second mode, operations mode, in the first mode operating parameters are downloadable from the computer to the memory and the patient use data is uploadable from the memory to the computer, in the second mode the operation of the orthosis device is controllable by the monitor system based on the operating parameters and the use of the orthosis device is monitorable by the monitor system and storable in the memory for downloading at a later date.

2. The physical therapy apparatus according to claim 1, wherein said first carriage member includes a first cuff on a first cuff arm for connecting said first cuff aim to a first body portion; said second carriage member includes a second cuff on a second cuff arm for connecting said second cuff arm to a second body portion.

3. The physical therapy apparatus according to claim 1, wherein said electrical ID comprises a resistor and the monitoring system includes an analog-to-digital converter for converting a voltage drop across said resistor to a digital signal uniquely identifying said orthosis device.

4. The physical therapy apparatus to claim 3 wherein said micro-controller is operable for selecting the at least one computer program based upon said digital signal.

5. The physical therapy apparatus according to claim 1, wherein said monitor system is detachably mounted to said orthosis device.

6. The physical therapy apparatus according to claim 1, wherein the patient sensors includes a temperature sensor mounted on said orthosis device for generating a temperature signal measurement, whereby said temperature sensor determines whether said orthosis device is being worn by a patient.

7. The physical therapy apparatus according to claim 1, wherein said first and second carriage members each include a cuff arm and a cuff for connecting said cuff arm to one of a first or second body portion of the patient; and each said cuff being slidably mounted on one of said cuff arms; and wherein the patient sensors include a temperature sensor mounted on one of said cuffs, whereby said temperature sensor determines whether said orthosis device is being worn by a patient.

8. The physical therapy apparatus according to claim 1, wherein said data communications interface is further adapted receiving parameters and commands from said computer.

9. The physical therapy apparatus according to claim 1, wherein the device sensors include a position sensor for detecting when a rotational movement of the first carriage member relative to the second carriage member has stopped, whereby said monitor system detects that the patient is holding a stretch in accordance with the operating parameter.

10. The physical therapy apparatus according to claim 9, wherein said monitor system includes a timing device for generating a patient detectable signal indicating a predetermined time period has expired since said position sensor means detected said stopping of movement of said first carriage member relative to said second carriage member.

11. The physical therapy apparatus according to claim 10, wherein said patient detectable signal comprises a noise generated by a buzzer.

12. The physical therapy apparatus according to claim 11, wherein said micro-controller is operable for counting the number of times said position sensor has detected said stops in movement of said first carriage member relative to said second carriage member and for notifying the patient an exercise session is over upon counting a predetermined number of said stops in movement.

13. The physical therapy apparatus according to claim 10, wherein the micro-controller and the memory are adapted for measuring and recording the extent of said movement of said first carriage member relative to said second carriage member.

14. The physical therapy apparatus according to claim 10, wherein the micro-controller and the memory are adapted for calculating and recording a measurement an angular relationship of said first carriage member relative to said second carriage member.

15. The physical therapy apparatus according to claim 14, wherein said micro-controller is operable for determining said angular relationship after said position sensor has detected said stops in movement of said first carriage member relative to said second carriage member.

* * * * *

UNITED STATES PATENT AND TRADEMARK OFFICE
CERTIFICATE OF CORRECTION

PATENT NO. : 7,182,738 B2 Page 1 of 1
APPLICATION NO. : 10/421965
DATED : February 27, 2007
INVENTOR(S) : Peter M. Bonutti It is certified that error appears in the above-identified patent and that said Letters Patent is hereby corrected as shown below:

Column 15, line 27    change "an" to --and--

Column 15, line 32    change "orthodic" to --orthotic--

Column 15, line 61    change "aim" to --arm--

Column 16, line 38    delete the word "means"

Column 16, line 58
the phrase    "for calculating and recording a measurement an angular"
should read    --for calculating and recording a measurement of an angular--

Signed and Sealed this

Fourth Day of September, 2007

JON W. DUDAS
*Director of the United States Patent and Trademark Office*